US008293213B2

(12) United States Patent
Schwartz et al.

(10) Patent No.: US 8,293,213 B2
(45) Date of Patent: Oct. 23, 2012

(54) METHOD AND APPARATUS FOR THROMBUS REMOVAL USING MAGNETIC PARTICLES

(75) Inventors: David Eric Schwartz, Menlo Park, CA (US); Scott A. Elrod, LaHonda, CA (US); Richard H. Bruce, Los Altos, CA (US); Daniel L. Larner, San Jose, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 618 days.

(21) Appl. No.: 12/403,124

(22) Filed: Mar. 12, 2009

(65) Prior Publication Data

US 2010/0233147 A1 Sep. 16, 2010

(51) Int. Cl.
*A61B 5/055* (2006.01)
*A61K 39/395* (2006.01)
*A61K 38/48* (2006.01)
*A61M 37/00* (2006.01)

(52) U.S. Cl. ............... 424/9.3; 424/9.34; 424/94.63; 424/94.64; 424/178.1; 424/489; 424/490; 424/491; 600/12

(58) Field of Classification Search .................. None
See application file for complete search history.

(56) References Cited

U.S. PATENT DOCUMENTS

| 4,141,687 | A | | 2/1979 | Forrest et al. | |
|---|---|---|---|---|---|
| 6,482,436 | B1 | * | 11/2002 | Volkonsky et al. | 424/489 |
| 6,638,494 | B1 | * | 10/2003 | Pilgrimm | 424/9.323 |
| 6,979,466 | B2 | * | 12/2005 | Lesniak et al. | 424/490 |
| 7,502,640 | B2 | * | 3/2009 | Conolly et al. | 600/411 |
| 2003/0105382 | A1 | * | 6/2003 | Brown et al. | 600/12 |
| 2006/0142632 | A1 | * | 6/2006 | Meretei | 600/12 |
| 2010/0055042 | A1 | * | 3/2010 | Yathindranath et al. | 424/9.36 |
| 2011/0071335 | A1 | * | 3/2011 | Ueda et al. | 600/12 |

OTHER PUBLICATIONS

Wu, Sau-Ching, et al., "Functional Production and Characterization of a Fibrin-Specific Single-Chain Antibody Fragment from Bacillus subtilis: Effects of Molecular Chaperones and a Wall-Bound Protease on Antibody Fragment Production," Applied and Environmental Microbiology, Jul. 2002, p. 3261-3269, American Society for Microbiology, 2002.
Chen, Haitao, et al., "Capture of magnetic carriers within large arteries using external magnetic fields," Journal of Drug Targeting, May 2008, 16:4, 262-268.

* cited by examiner

*Primary Examiner* — David A Saunders
(74) *Attorney, Agent, or Firm* — Marger Johnson & McCollom, P.C.

(57) ABSTRACT

A method and system for affecting a thrombus after ischemic stroke. The method may include injecting a plurality of magnetic particles into a bloodstream and moving or distorting a thrombus formed or lodged in the bloodstream using a magnetic force to manipulate the magnetic particles. The method may include conjugating ferromagnetic particles, paramagnetic particles, or superparamagnetic particles to a thrombus-specific attachment agent such as an anti-fibrin antibody, and injecting the conjugated particles into the bloodstream. Thereafter, the thrombus may be agitated, broken apart, or dissolved using a magnetic field to exert a magnetic force on the conjugated particles. The method may also include injecting a thrombolytic agent into the bloodstream to interact with and further dissolve the thrombus.

15 Claims, 12 Drawing Sheets

METHOD AND APPARATUS FOR THROMBUS REMOVAL USING MAGNETIC PARTICLES

BACKGROUND

Rapid removal of a thrombus (i.e., blood clot) after ischemic stroke can greatly reduce the risk of the loss of brain function. Conventional treatment for removing the thrombus includes pharmacology and surgery. Tissue plasminogen activator (tPA), a pharmaceutical, has been shown to help dissolve blood clots. Other drugs, including streptokinase and urokinase, have also been used. However, these drugs can take several hours to be effective.

Qualified specialists may use certain procedures in an effort to enhance the effectiveness of the tPA or to physically remove the thrombus. For example, the qualified specialists may use ultrasound, which enhances the efficacy of the therapy. The ultrasound can be applied either intravenously via laparoscopic catheterization or externally. The blood clot can also be mechanically removed using a system called Mechanical Embolus Removal in Cerebral Ischemia (MERCI®). But each of these approaches requires highly specialized training. Hospitals have limited resources, and therefore, may not have the financial means for the necessary training and staffing of qualified specialists. As a result, such qualified specialists may not be available at all hospitals.

In addition, even when the qualified specialists are available, several hours often lapse between the stroke and the start of such procedures—resulting in valuable time lost—ultimately to the detriment or even death of the patient. Consequently, a system for thrombolysis that could easily be applied by an emergency room physician or physician's assistant would improve treatment and potentially save lives.

DETAILED DESCRIPTION OF THE EMBODIMENTS

Embodiments discussed here relate to a method and system for thrombolysis using magnetic forces to affect a thrombus, commonly known as a blood clot. While particularly suited for use after ischemic stroke, the method and system disclosed herein can also be used as a preventive measure or to treat other related or unrelated medical conditions. Magnetic particles may be conjugated to biomolecules allowing specific attachment to thrombus tissue. The magnetic particles may comprise ferromagnetic, paramagnetic, or superparamagnetic nanoparticles, or particles with another type of magnetism, such as diamagnetism. Preferably, superparamagnetic nanoparticles are used, which are defined herein as ferromagnetic materials of small enough size that their magnetization is not retained in the absence of an external magnetic field. For the sake of brevity, reference will generally be made herein to "magnetic particles," although it should be understood that the term "magnetic particles" can refer to any of the types of magnetic particles mentioned above. The magnetic particles can be conjugated to a thrombus-specific attachment agent such as an anti-fibrin antibody. One example of a suitable anti-fibrin antibody is a monoclonal antibody known as MH-1. Detailed procedures for manufacturing MH-1 are set forth in Wu, Sau-ching, et al., Applied and Environmental Microbiology, Vol 86, No. 3, July 2002, pp 3261-3269. The term 'conjugated' as used here means united or coupled.

An operator, such as a physician or physician's assistant, may inject the magnetic particles, typically conjugated to anti-fibrin antibodies, into a bloodstream of a person having suffered ischemic stroke, which causes the magnetic particles to flow through the bloodstream and to congregate about the tissue of the thrombus. The injection may include a shot or an intravenous (IV) application, among other possibilities, and may be administered continuously or intermittently. A shot generally provides a larger concentration at one time at a targeted location, whereas an IV tends to provide a more dilute application into the bloodstream but over a longer period of time. Subsequently, the operator may cause or create a static or moving magnetic field. Preferably, the static or moving magnetic field is generated external to the patient's body and constructed and arranged to penetrate beneath a surface of the patient's body to the region of the thrombus. A magnetic force can be effected upon the magnetic particles, for example, by a static magnetic field, in the case of ferromagnetic particles, or by the gradient of a non-uniform static magnetic field, in the case of paramagnetic or superparamagnetic particles.

The operator may direct the magnetic field to agitate or move the magnetic particles so that the thrombus is agitated or moved, even to the point of the thrombus being broken apart or dissolved. This allows blood to resume flowing in the bloodstream, or may serve to increase the flow of blood in the bloodstream. The magnetic field may also be used to trap the magnetic particles at or about the thrombus or to hold the particles in place. In addition, the thrombus can be moved to a different location where a blood vessel is wider, to allow blood flow or increased blood flow.

In some example embodiments, the operator may create the moving magnetic field by causing a physical displacement of magnets to manipulate the magnetic particles, resulting in the agitation of the thrombus. Alternatively, an electromagnet or a bank of electromagnets may create the moving magnetic field through the variation of electrical signals to generate varying magnetic forces to manipulate the magnetic particles. Persons with skill in the art will recognize that other approaches for generating static or moving magnetic fields or varying magnetic forces can also be used.

In addition, the operator may also apply a thrombolytic agent such as tissue plasminogen activator (tPA) to the thrombus in various ways. For example, the tPA may be applied (a) by co-attachment to one or more of the magnetic particles, (b) by independent conjugation to a thrombus-specific attachment agent, or (c) by direct injection to the bloodstream, among other possibilities. The agitation of the magnetic particles, with or without the thrombolytic agent, can move or break apart the thrombus. In addition, the agitation of the magnetic particles can make the thrombolytic agent more effective at dissolving the thrombus.

In any of the embodiments mentioned herein, the magnetic particles can be manipulated in various ways including, but not limited to, application of a unidirectional magnetic force to compress the thrombus to allow blood flow to resume, pulsing a magnetic force to break apart the thrombus, oscillating the magnetic force to align a polarity of the magnetic particles so that they spin, or otherwise moving the thrombus.

Figure 1:
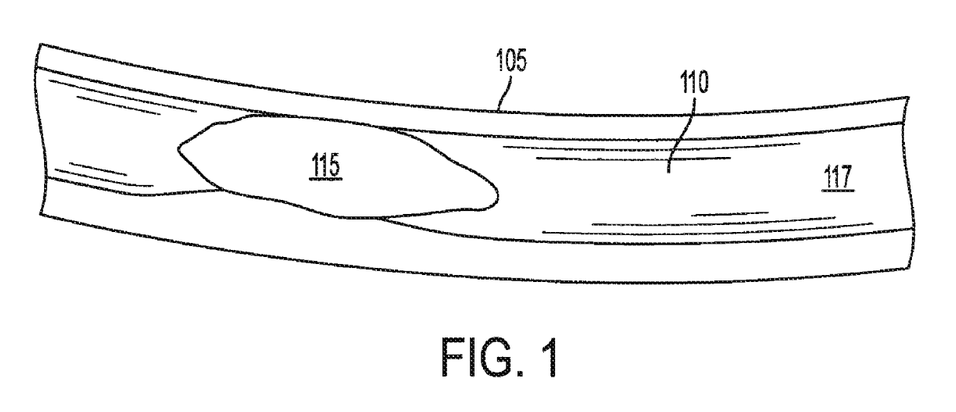
FIG. 1 shows a thrombus lodged in a lumen of a blood vessel.

FIG. 1 shows a thrombus 115 formed or lodged in a lumen 110 of a blood vessel 105. The lumen 110 is the hollow interior of the blood vessel 105 in which blood 117 flows. The blood vessel 105 may be an artery or a vein. Although one shape of the thrombus 115 is shown for exemplary purposes, the thrombus 115 may take the form of any shape or size within the lumen 110 of the blood vessel 105. The presence of the thrombus 115 impedes the flow of the blood 117.

Figure 2:
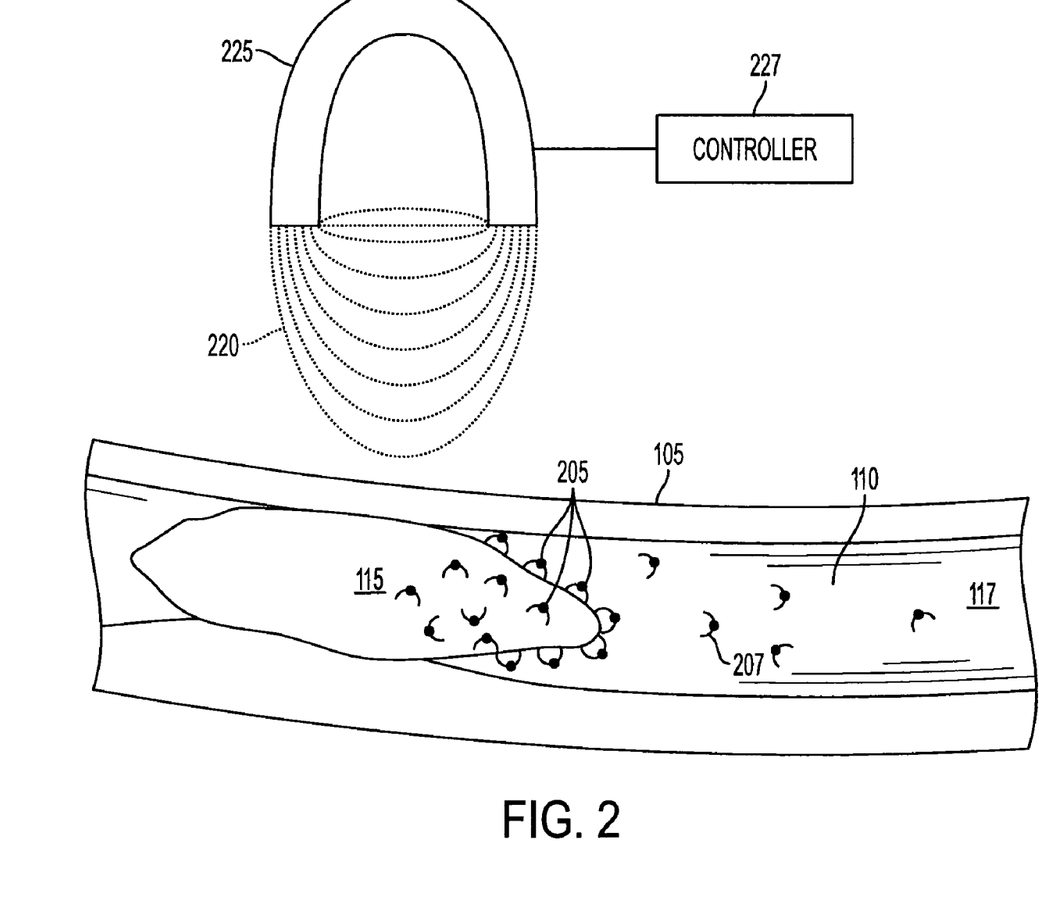
FIG. 2 shows an example of magnetic particles conjugated to anti-fibrin antibodies in the lumen of the blood vessel located about the thrombus and a magnet located external to the blood vessel.

FIG. 2 shows an example of magnetic particles 205 conjugated to anti-fibrin antibodies 207 in the lumen 110 of the blood vessel 105 located about the thrombus 115, and in addition, a magnet 225 located external to the blood vessel 105, the magnet having a magnetic field 220 and moved using controller 227.

Although the magnet 225 is illustrated as a permanent magnet, such permanent magnet is exemplary, and it should be understood that magnet 225 can be an electromagnet or a permanent magnet, moving or stationary. Where the magnet 225 is an electromagnet, the controller 227 may vary an electrical signal associated with the electromagnetic field 220 to control the electromagnetic force. Further, while generally referred to herein as "a magnet" and "a magnetic field," there may be one or more magnets 225 or one or more magnetic fields 220. The magnet 225 is preferably located external to a patient's body and may generate the magnetic field external to the patient's body, but with enough force to penetrate beneath a surface of the patient's body to the region of the thrombus 115. Also, as previously mentioned, the magnetic particles 205 may include ferromagnetic, paramagnetic, or superparamagnetic nanoparticles, or particles with another type of magnetism, such as diamagnetism; although for the sake of brevity, these will generally be referred to herein as merely "magnetic particles 205."

Prior to injecting the magnetic particles 205 into blood 117 of the blood vessel 105, drug manufacturers may prefabricate the magnetic particles 205 at a location separate from a hospital, such as at a drug production facility. The drug manufacturers may conjugate the magnetic particles 205 to one or more thrombus specific attachment agents such as, for example, one or more anti-fibrin antibodies 207. As mentioned above, one example of an anti-fibrin antibody is MH-1, although other types of anti-fibrin antibodies may be used. If the magnetic particles 205 are superparamagnetic nanoparticles, for example, then the drug manufacturer may conjugate the superparamagnetic nanoparticles 205 in a similar fashion. For the sake of brevity, when referring to the magnetic particles 205, such reference may include any of the types of magnetic particles previously discussed, and may also include anti-fibrin antibodies conjugated therewith.

Once at the hospital or other medical clinic, the operator may inject the magnetic particles 205 into the blood 117 of the blood vessel 105, either continuously or intermittently. Persons with skill in the art will recognize that the injection may occur in a bloodstream connected to blood vessel 105, and need not require an injection directly into blood vessel 105. After the magnetic particles 205 are injected into the blood 117, the magnetic particles 205 may congregate, or in other words be located about, tissue of the thrombus 115. In some embodiments, the anti-fibrin antibodies of the magnetic particles 205 may cause the particles to attach to proteins (not shown) of the thrombus 115. In another embodiment, the magnetic field 220 of the magnet 225 may trap the magnetic particles 205 about the thrombus or hold the magnetic particles 205 in place using a magnetic force exerted by the magnetic field 220. The operator may wait a predefined period of time until the magnetic particles 205 are trapped or located about the thrombus 115. While FIG. 2 shows the magnetic particles 205 attaching to a portion of the thrombus 115, in other embodiments, the magnetic particles 205 may attach to substantially all of the thrombus 115.

After the magnetic particles 205 are located about the thrombus 115, the operator may then affect the thrombus 115 using the magnetic field 220, which exerts a magnetic force to manipulate the magnetic particles 205 in the blood 117. The thrombus 115 may be moved or distorted so that the blood 117 may resume flowing in the blood vessel 105, or may generally serve to increase the flow of blood 117 in the bloodstream associated with the blood vessel 105, or to a particular portion of the patient's body (not shown). In addition, the thrombus 115 can be moved to a different location where the blood vessel 105 is wider, to allow blood flow or increased blood flow. These and other details of how the magnetic field 220 can affect the thrombus 115 are further described in detail below.

Figure 3:
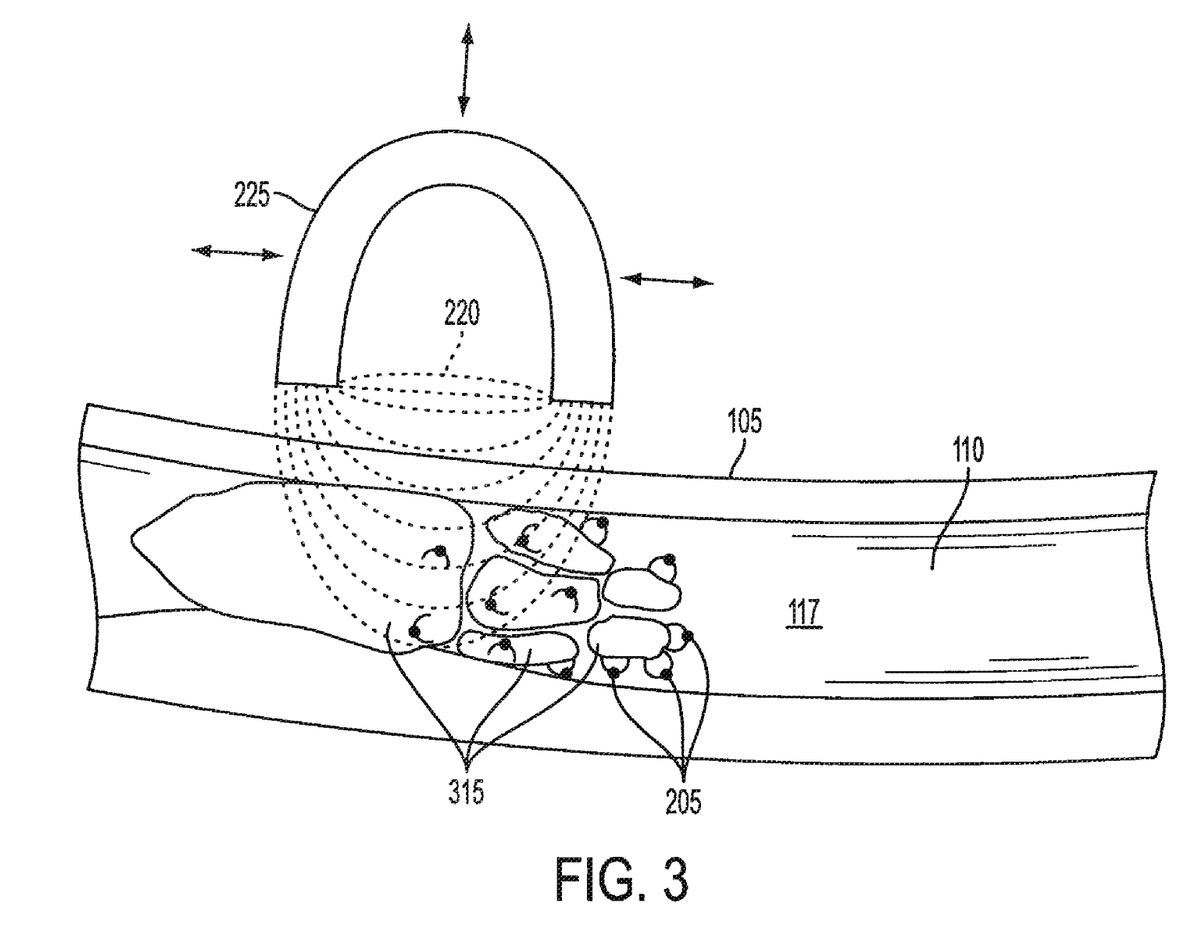
FIG. 3 shows an example of a magnet moved in proximity to the blood vessel.

FIG. 3 shows an example of the magnet 225 moved in proximity to the blood vessel 105 to exert a magnetic force on the magnetic particles 205 to break apart the thrombus 115 by manipulating the magnetic particles 205 located about the thrombus 115.

The operator may break apart the thrombus 115 into a plurality of thrombus portions 315 by manipulating the magnetic particles 205 located about the thrombus 115. The magnet 225 having the magnetic field 220 may be moved in proximity to the blood 117 or the thrombus 115 to exert the magnetic force on the magnetic particles 205. While FIG. 3 shows a physical displacement of magnet 225 and magnetic field 220, such physical displacement is exemplary, and it should be understood that an electromagnet 225 can be used to modulate an electromagnetic field 220 using controller 227 without physically displacing the electromagnet 225. The operator may cause the magnet 225 or the associated magnetic field 220 to be moved in any direction to further affect the breaking apart of the thrombus 115. In addition, a static magnetic field 220 may also be applied to the magnetic particles 205. For example, a static magnetic field 220 may be applied in the case where the magnetic particles 205 comprise ferromagnetic particles. As another example, a gradient of a non-uniform static magnetic field 220 may be applied in the case where the magnetic particles 205 comprise paramagnetic or superparamagnetic particles. Preferably, the magnet 225 and the associated magnetic fields 220 are arranged in a manner to move, distort, compress, break apart, or dissolve the thrombus 115. Either a portion or the entire thrombus 115 may be dissolved.

The magnet 225 may be one or more electromagnets 225 or one or more superconducting electromagnets 225. Further, the magnetic field 220 may be an electromagnetic field 220 that exerts an electromagnet force on the magnetic particles 205. The operator may cause a variation of an electrical signal using controller 227 associated with the electromagnetic field 220 to control the associated electromagnetic force on the magnetic particles 205. In one example, the magnetic force exerted on the magnetic particles 205 may be a unidirectional magnetic force applied to the magnetic particles 205 to compress the thrombus to allow the blood 117 to resume flowing.

In another example, an electrical signal (not shown) associated with the electromagnetic field 220 may be pulsed by the controller 227 so that the electromagnetic force is likewise pulsed. In yet another example, an electrical signal (not shown) associated with the electromagnetic field 220 may be oscillated by the controller 227 to align a polarity of each of the magnetic particles 205 so that the magnetic particles 205 spin. In any of the embodiments mentioned herein, the thrombus 115 may be broken apart into portions 315 responsive to an electromagnetic force.

Figure 4:
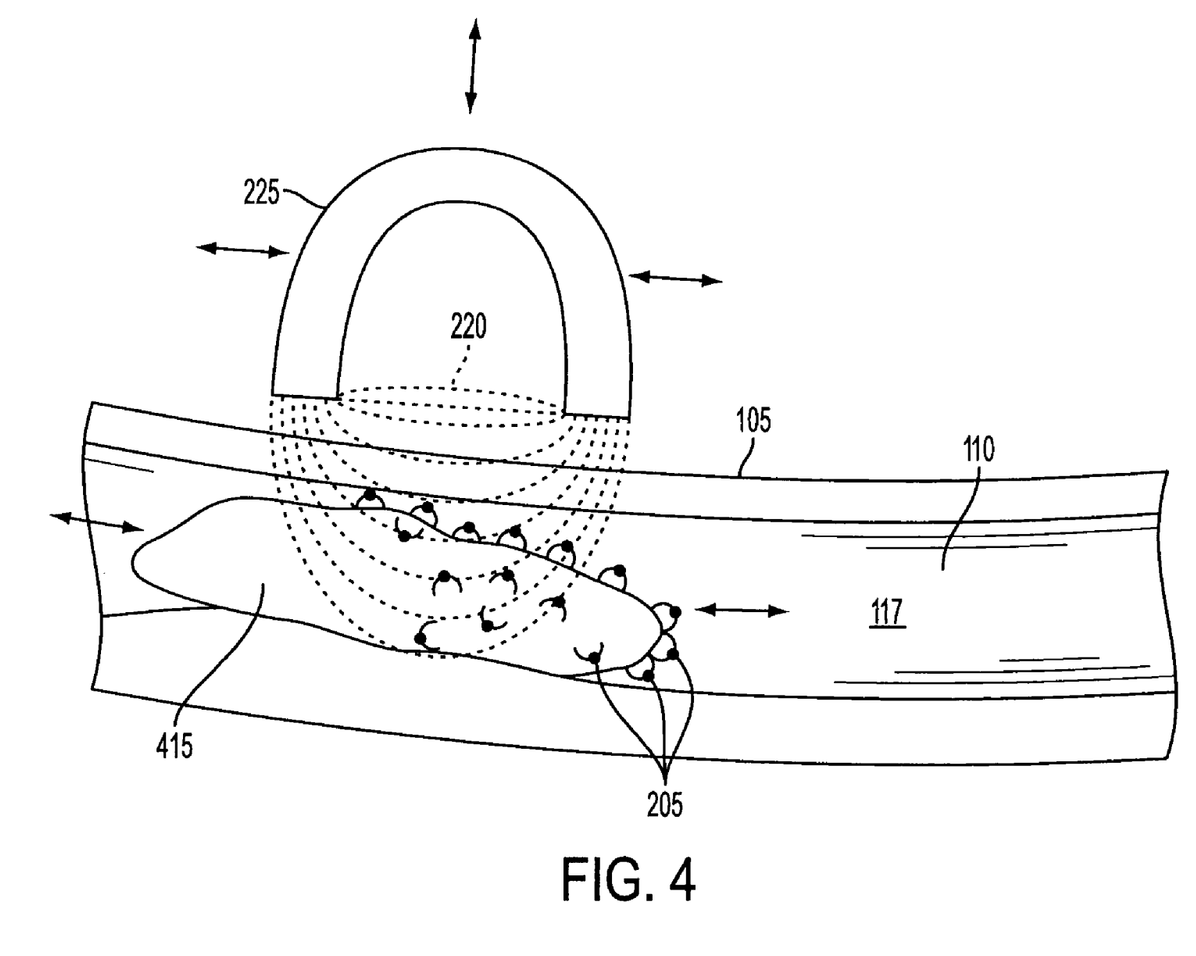
FIG. 4 shows an example of a magnet having a magnetic field to exert a unidirectional magnetic force to the magnetic particles located about the thrombus.

FIG. 4 shows an example of a magnet 225 having a magnetic field 220 to exert a unidirectional magnetic force to the magnetic particles 205 located about the thrombus 415 to compress the thrombus 415, thereby allowing blood 117 to resume flowing in the blood vessel 105, according to another embodiment.

Application of a unidirectional magnetic force from the magnet 225 through the blood vessel 105 so as to interact with the magnetic particles 205 can serve to move or compress the thrombus 415 to allow blood 117 to resume flowing in the blood vessel 105, or to increase the flow of blood 117 in the bloodstream or to a particular portion of the patient's body. The operator may cause the magnet 225 or the associated magnetic field 220 to be moved in any direction to further compress or move the thrombus 415.

Figure 5:
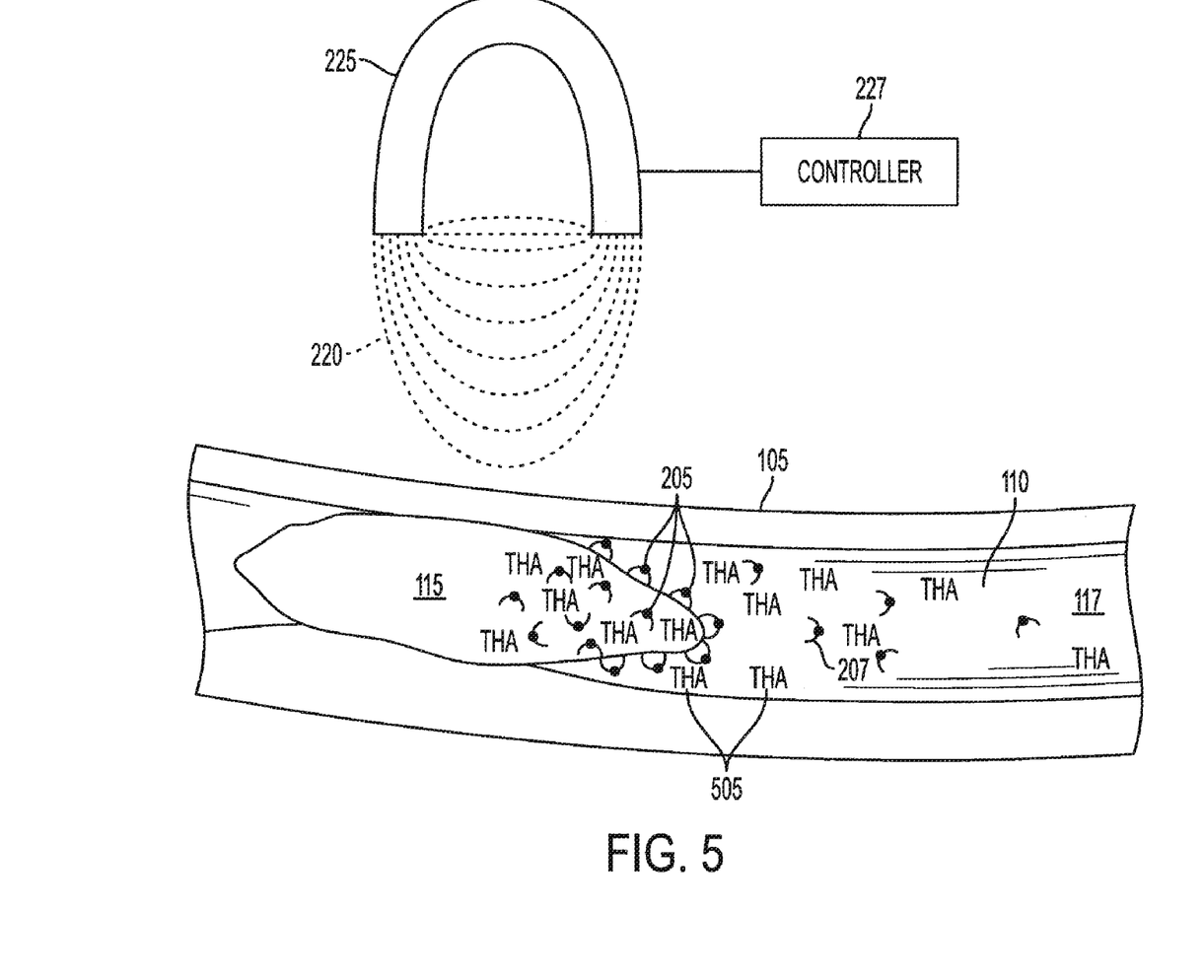
FIG. 5 shows an example of magnetic particles conjugated to anti-fibrin antibodies and a thrombolytic agent in the lumen of the blood vessel located about the thrombus and a magnet located external to the blood vessel.

FIG. 5 shows an example of magnetic particles 205 conjugated to anti-fibrin antibodies 207 and a thrombolytic agent (referred to in the figures and herein by a general designation of "THA") in the lumen 110 of the blood vessel 105 located about the thrombus 115, and in addition, a magnet 225 located external to the blood vessel 105, the magnet 225 having a magnetic field 220 and moved using controller 227.

In addition to magnetic particles 205, a thrombolytic agent THA may also be applied to the thrombus 115 to further facilitate the dissolution of the thrombus 115. The thrombolytic agent THA may comprise, for example, tissue plasminogen activator (tPA), streptokinase, or urokinase, among other suitable agents. While FIG. 5 shows THA to represent the thrombolytic agent, such term is inclusive of tPA, streptokinase, or urokinase, among other suitable agents.

The operator may apply the thrombolytic agent THA to the thrombus 115 in various ways, either continuously or intermittently. For example, the thrombolytic agent THA may be applied (a) by co-attachment to one or more of the magnetic particles 205, (b) by independent conjugation to a thrombus-specific attachment agent (not shown), or (c) by direct injection into blood 117 of a bloodstream associated with blood vessel 105, among other possibilities.

The operator may inject the thrombolytic agent THA in the blood 117 to interact with the thrombus 115. The injection may be accomplished using a shot or an intravenous (IV) application, among other possibilities. The thrombolytic agent THA may be administered separately or in the same shot or IV as the magnetic particles 205. In some circumstances, the operator may prefer to concentrate the thrombolytic agent THA at one time to a targeted location using a shot; whereas in other circumstances, the operator may prefer to use an IV, which tends to provide a more dilute application into the bloodstream but over a longer period of time.

Further, the thrombolytic agent THA may be conjugated to a thrombus-specific attachment agent (not shown) different from or the same as the thrombus-specific attachment agent used for the magnetic particles 205. In some example embodiments, the thrombolytic agent THA may be co-attached to one or more of the magnetic particles 205 themselves, which may then attach to proteins (not shown) of the thrombus 115.

Figure 6:
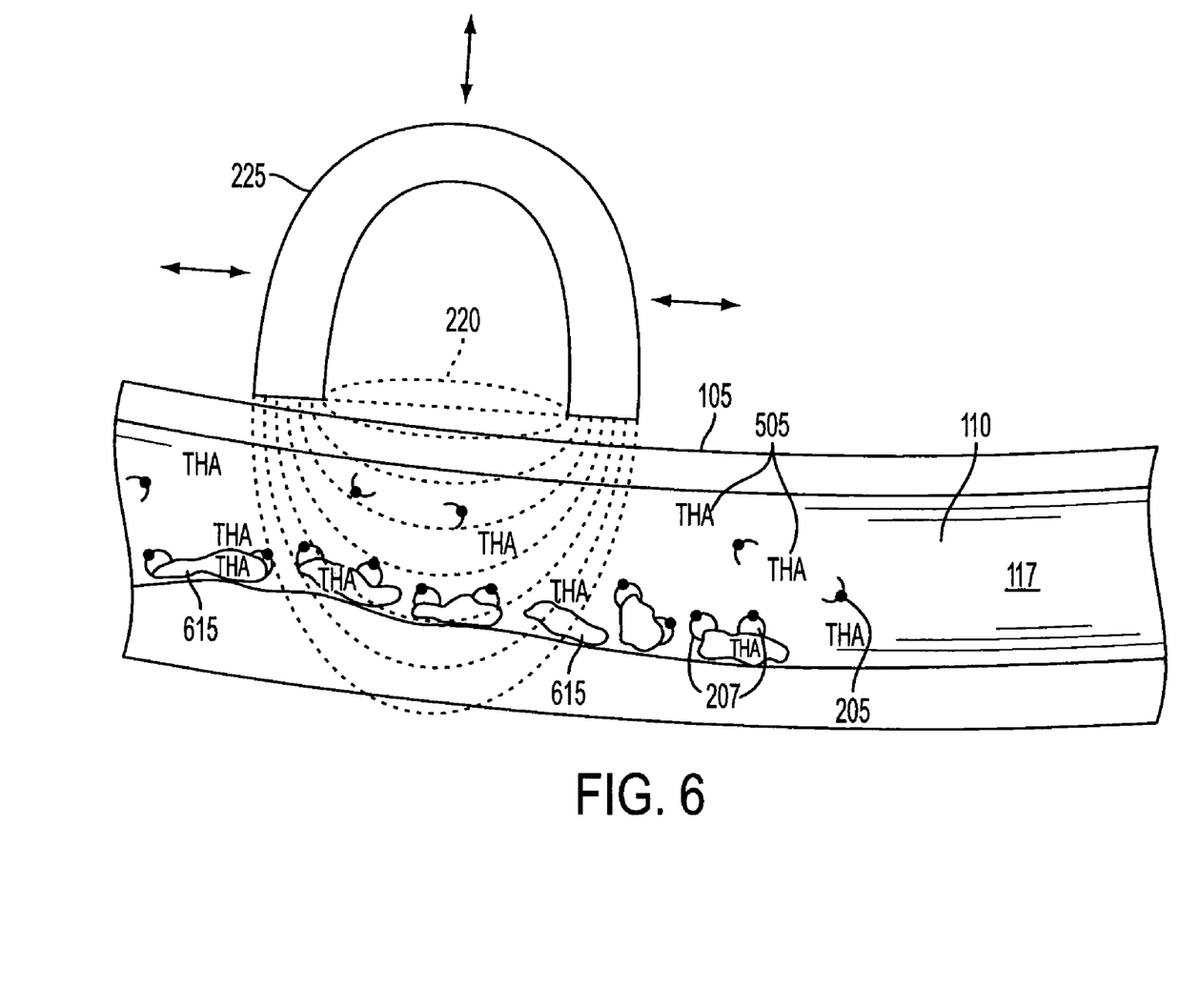
FIG. 6 shows an example of a magnet moved in proximity to the blood vessel.

FIG. 6 shows an example of the magnet 225 moved in proximity to the blood vessel 105 to exert a magnetic force on the magnetic particles 205 to agitate and dissolve the thrombus 115 into dissolved portions 615, according to yet another embodiment.

After injecting the thrombolytic agent THA and the magnetic particles 205, the operator may agitate the thrombus 115 using the magnetic force and the thrombolytic agent THA until the thrombus 115 is either partially or completely dissolved. In other words, by agitating the thrombus 115, or by agitating the surface of the thrombus 115, the thrombolytic agent THA may be mixed around in the blood 117, which can increase the ability of the thrombolytic agent THA to dissolve the thrombus 115. The thrombolytic agent THA may dissolve the thrombus 115 while the manipulated magnetic particles 205 agitate and move the thrombus 115. For example, the thrombus 115 can be moved to a different location where the blood vessel 105 is wider, to allow blood 117 to flow or to increase its flow. When held in this different location, the thrombolytic agent THA can more effectively dissolve the thrombus 115 because the thrombus 115 may be more accessible. Not only is the thrombus 115 more accessible, but the existence of blood flow allows more time for thrombolytic agent THA to work on the thrombus 115 without the patient incurring excessive tissue damage dying.

Although FIG. 6 shows a physical displacement of magnet 225 and magnetic field 220, such physical displacement is exemplary, and it should be understood that one or more electromagnets 225 can be used to modulate an electromagnetic field 220 using controller 227 without physically displacing the electromagnet 225. As previously mentioned, the magnetic field 220 may be an electromagnetic field 220 that exerts an electromagnet force on the magnetic particles 205. The operator (or an electromagnetic machine itself) may cause a variation of an electrical signal using controller 227 associated with the electromagnetic field 220 to control the associated electromagnetic force on the magnetic particles 205. The controller 227 can also include turning on and off one or more electromagnets sequentially, simultaneously, or in another pattern.

Such control can include, for example, varying, pulsing, or oscillating the electrical signal so that the electromagnetic force acts on the magnetic particles 205 in such a way as to increase the rate of dissolution of the thrombus 116 into dissolved portions 615. This allows the blood 117 to resume flowing in the blood vessel 105, or may generally serve to increase the flow of blood 117 in the bloodstream associated with the blood vessel 105, or to a particular portion of the patient's body (not shown).

Figure 7:
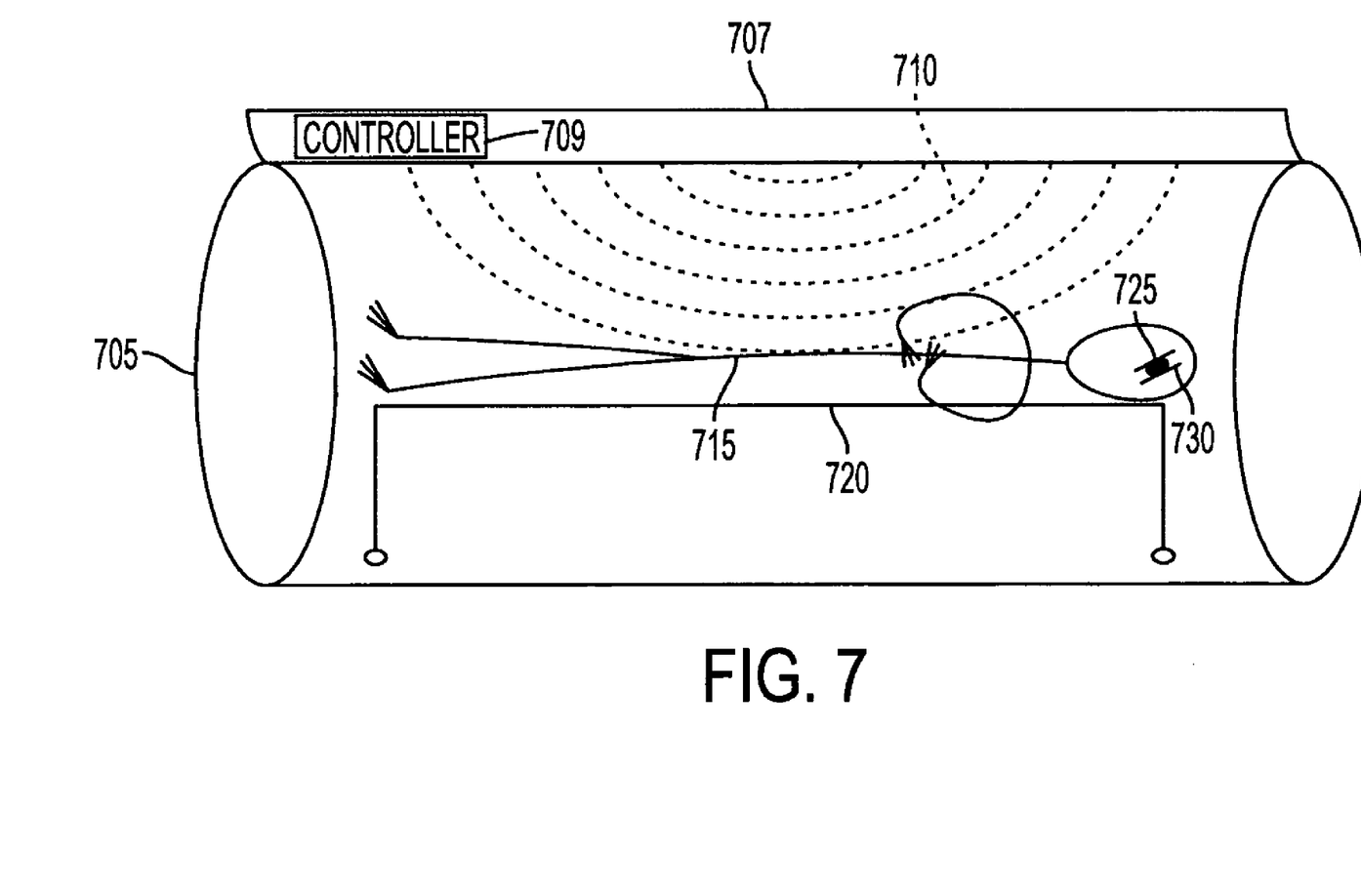
FIG. 7 shows an example of a system including a chamber comprising an electromagnet that can emit electromagnetic fields toward a person within the chamber.

FIG. 7 shows an example of a system including a chamber 705 comprising an electromagnet 707 that can emit electromagnetic fields 710 toward a person 715 within the chamber 705, the patient 715 having a thrombus 725 formed or lodged in a blood vessel 730 and magnetic particles injected into the blood thereof, according to still another embodiment.

The operator may direct the patient 715 to be positioned on support member 720 and inserted into the chamber 705. Persons having skill in the art will recognize that the chamber 705 may come in many different forms or shapes, and may enclose the patient 715 without the patient 715 needing to be inserted into the chamber 705. The chamber may have coupled thereto an electromagnet 707 controlled by controller 709. The electromagnet 707 may create magnetic fields 710 through the variation of electrical signals using controller 709 to generate varying magnetic forces to manipulate the magnetic particles.

While FIG. 7 shows the electromagnet 707 attached to an upper portion of the chamber 705, it should be understood that the electromagnet 707 may be coupled to any portion of the chamber 705 and may comprise all or some of the interior or exterior of the chamber 705. Moreover, although FIG. 7 shows electromagnetic fields 710 emanating from the electromagnet 707 in a particular pattern, it should be understood that such pattern is exemplary and electromagnetic fields 710 may emanate from any direction toward the patient 715. In some embodiments, the chamber 705 and electromagnet 707 may be associated with an magnetic resonance imaging (MRI) device. For example, an MRI device or a modified MRI device may be used to generate magnetic fields 710 to exert a magnetic force into the patient 715 to manipulate the magnetic particles 205 to affect the thrombus 725 in various ways similar to those described above.

The patient 715 may have a thrombus 725 formed or lodged in blood vessel 730. Although FIG. 7 shows the thrombus 725 and blood vessel 730 located in the head of the patient 715, the thrombus 725 and blood vessel 730 may be located in any area of the body of patient 715.

Any of the techniques or aspects of the elements discussed above may be used with the embodiment shown in FIG. 7, including the injection of conjugated magnetic particles 205 into the patient 715, the injection of a thrombolytic agent THA (e.g., tPA) into the patient 715, the manipulation of the magnetic particles 205 in combination with the dissolution of the thrombus 725 using the magnetic fields 710 to exert a magnetic force, and the dissolution of the thrombus using the thrombolytic agent, among the other inventive aspects as discussed above. Therefore, a detailed discussion of these aspects will not be repeated.

Figure 8:
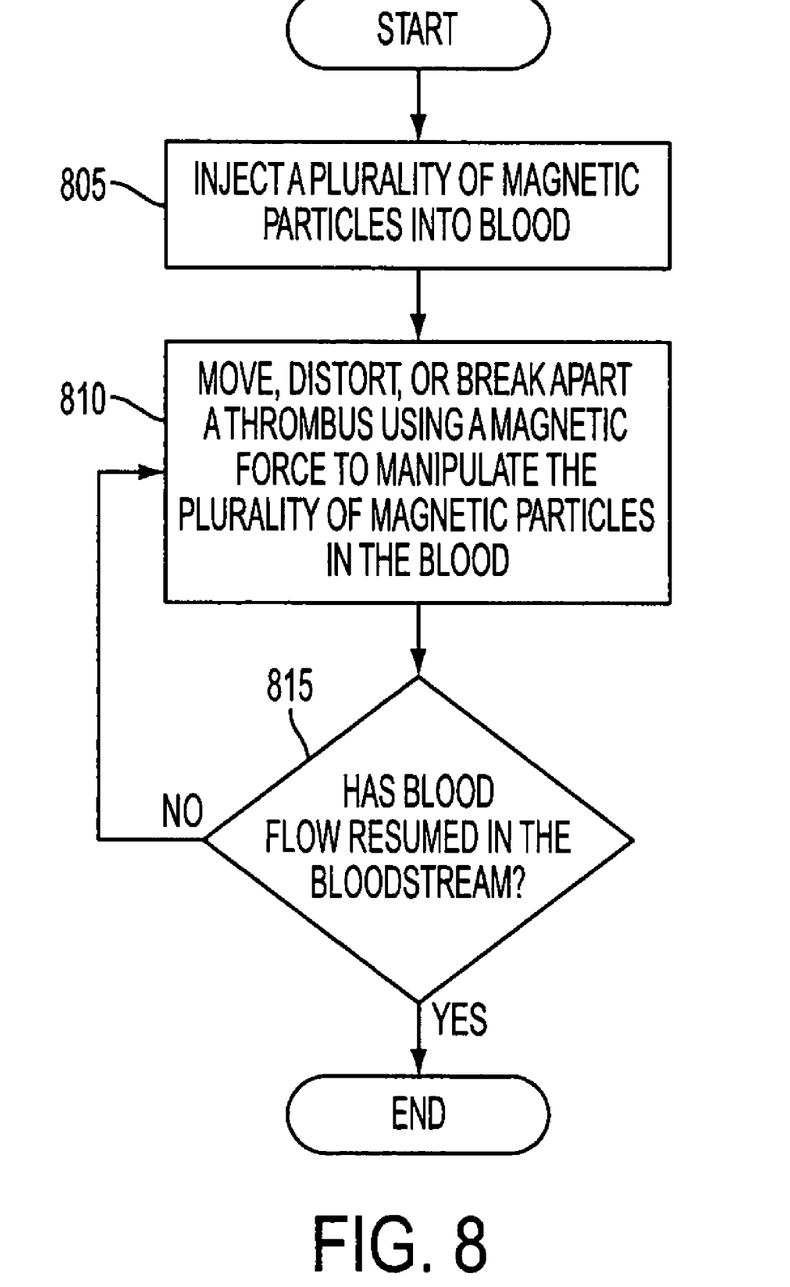
FIG. 8 shows a flow diagram illustrating an embodiment of a thrombolysis technique.

FIG. 8 shows a flow diagram illustrating a thrombolysis technique according to some embodiments of the invention. At 805, the operator may inject a plurality of magnetic particles either continuously or intermittently into blood (e.g., a bloodstream) of a patient. Preferably, the magnetic particles are injected continuously through an IV. The operator may then move, distort, or break apart a thrombus (i.e., blood clot) at 810 using a magnetic force to manipulate the plurality of magnetic particles in the blood. A determination can then be made whether the blood flow has resumed in the bloodstream at 815. If it is determined that the blood flow has resumed, the procedure may end. Otherwise, additional moving, distorting, or breaking apart of the thrombus at 810 may be continued.

Figure 9:
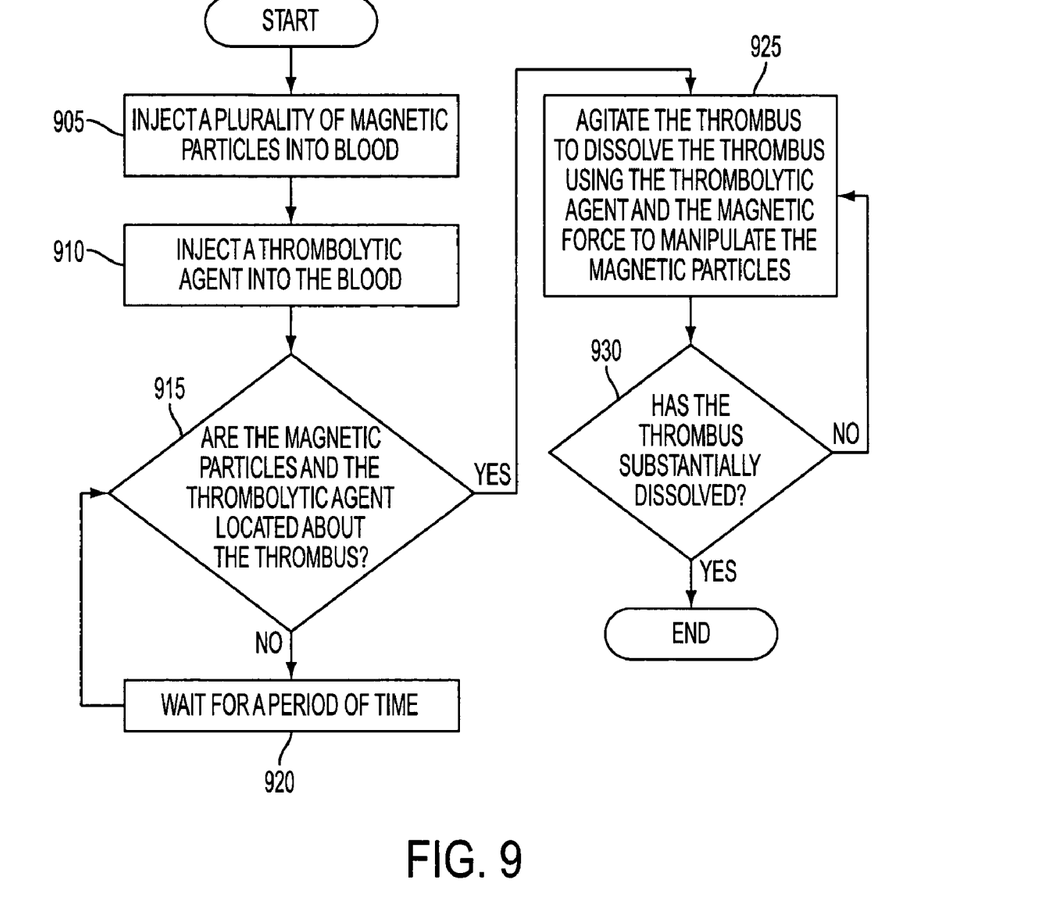
FIG. 9 shows a flow diagram illustrating another embodiment of a thrombolysis technique.

FIG. 9 shows a flow diagram illustrating another thrombolysis technique according to some embodiments. At 905, the operator may inject a plurality of magnetic particles either continuously or intermittently into blood (e.g., a bloodstream) of a patient. Preferably, the magnetic particles are injected continuously through an IV. At 910, the operator may inject a thrombolytic agent THA, such as tPA, streptokinase, or urokinase, into the bloodstream in either a continuous or intermittent fashion. Preferably, the THA is injected continuously through an IV. While FIG. 9 shows 905 and 910 as separate boxes, persons having skill in the art will recognize that 905 and 910 can be combined into a single step.

At 915, a determination can be made whether the magnetic particles and the thrombolytic agent are located about the thrombus. If it is determined that they are not sufficiently located about the thrombus, the operator may wait for a period of time at 920, after which the determination at 915 can again be made. Alternatively, an inference can be made that after a predefined period of time, the magnetic particles and the thrombolytic agent are assumed to be located about the thrombus, without making an affirmative determination of such, and the method may then proceed to 925.

Once a sufficient amount (e.g., enough to effectuate the breaking apart or dissolution of the thrombus) of magnetic particles and thrombolytic agent are located about the thrombus, or an inference of such is made, the method proceeds to 925. At 925, the operator may agitate the thrombus to dissolve the thrombus using the thrombolytic agent and the magnetic force to manipulate the magnetic particles.

In other words, magnetic fields may exert a magnetic force to manipulate the magnetic particles, which may be coupled to the thrombus. The manipulation of the magnetic particles may agitate the thrombus and increase the rate of dissolution of the thrombus, which may further dissolve in the presence of the thrombolytic agent. At 930, a determination can be made whether the thrombus has substantially dissolved, and if so, the procedure may end. Otherwise, the procedure may return to 925 to agitate the thrombus further.

Figure 10:
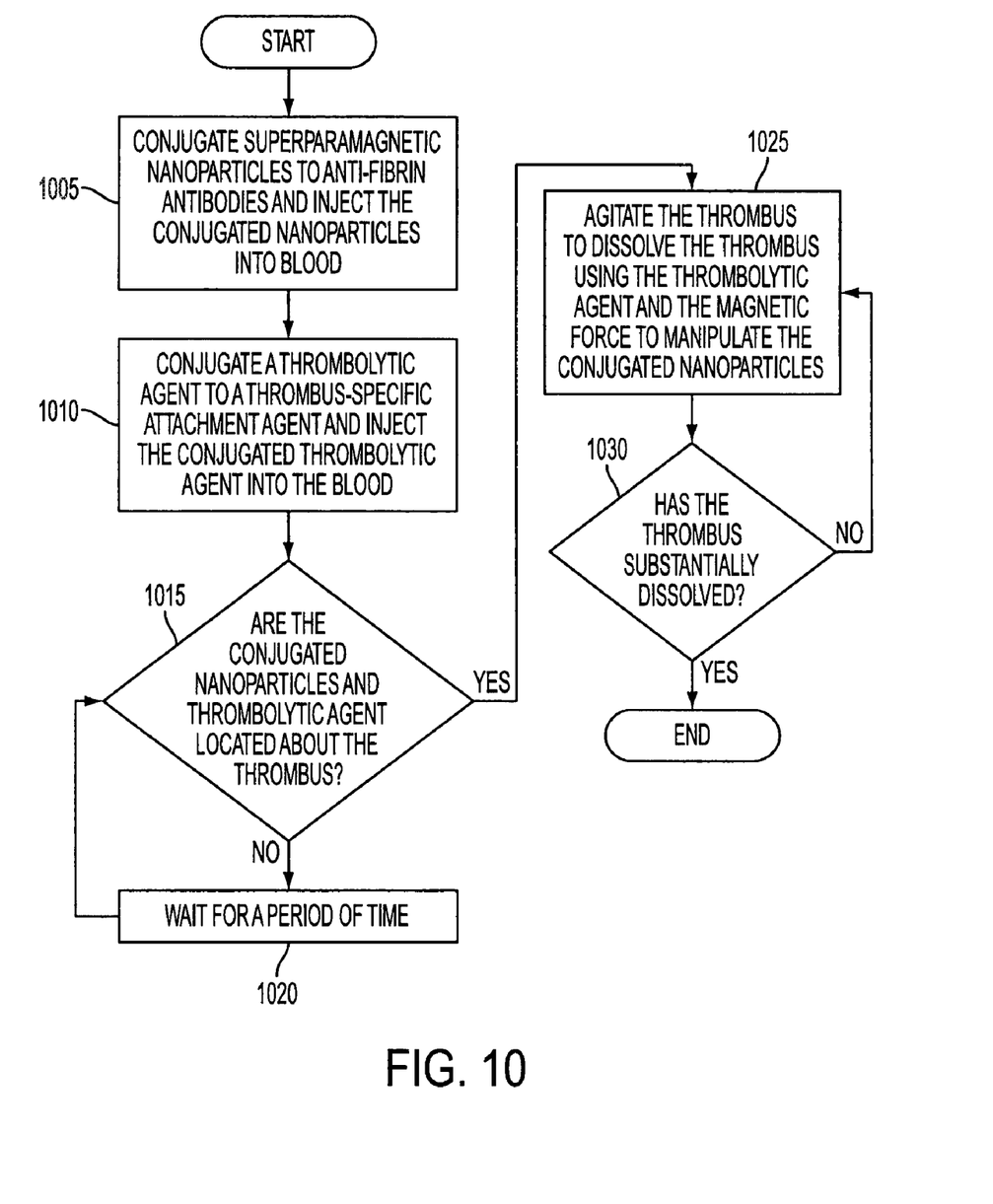
FIG. 10 shows a flow diagram illustrating another embodiment of a thrombolysis technique.

FIG. 10 shows a flow diagram illustrating yet another thrombolysis technique according to some embodiments. At 1005, a drug manufacturer may conjugate superparamagnetic nanoparticles, or other suitable magnetic particles, to anti-fibrin antibodies. The operator may inject the conjugated nanoparticles either continuously or intermittently into blood (e.g., a bloodstream) of a patient. Preferably, the conjugated nanoparticles are injected continuously through an IV. At 1010, the drug manufacturer may conjugate a thrombolytic agent to a thrombus-specific attachment agent. The operator may inject the conjugated thrombolytic agent either continuously or intermittently into the blood (e.g., the bloodstream). Preferably, the conjugated thrombolytic agent is injected continuously through an IV. The order of 1005 and 1010 shown in FIG. 10 is exemplary and it should be understood that the drug manufacturer will preferably prepare the conjugated nanoparticles and the conjugated thrombolytic agent before hand, and will typically ship these items to a hospital for use by the operator.

A determination can be made at 1015 whether the conjugated nanoparticles and thrombolytic agent are located about the thrombus. If a sufficient amount (i.e., enough to effectuate the breaking apart of dissolution of the thrombus) of the conjugated nanoparticles and thrombolytic agent are located about the thrombus, the method proceeds to 1025. Otherwise, the operator may wait for a period of time at 1020, after which the determination at 1015 can again be made. Alternatively, an inference can be made that after a predefined period of time, the conjugated nanoparticles and the thrombolytic agent are assumed to be located about the thrombus, without making an affirmative determination of such, and the method may then proceed to 1025.

At 1025, the operator may agitate the thrombus to dissolve the thrombus using the thrombolytic agent and the magnetic force to manipulate the conjugated nanoparticles. In other words, electromagnetic fields may exert an electromagnetic force to manipulate the conjugated superparamagnetic nanoparticles, which may be coupled to the thrombus.

The manipulation of the conjugated superparamagnetic nanoparticles may agitate the thrombus and increase the rate of dissolution of the thrombus, which may further dissolve in the presence of the thrombolytic agent. At 1030, a determination can be made whether the thrombus has substantially dissolved, and if so, the procedure may end. Otherwise, the procedure may return to 1025 to agitate the thrombus further.

Figure 11:
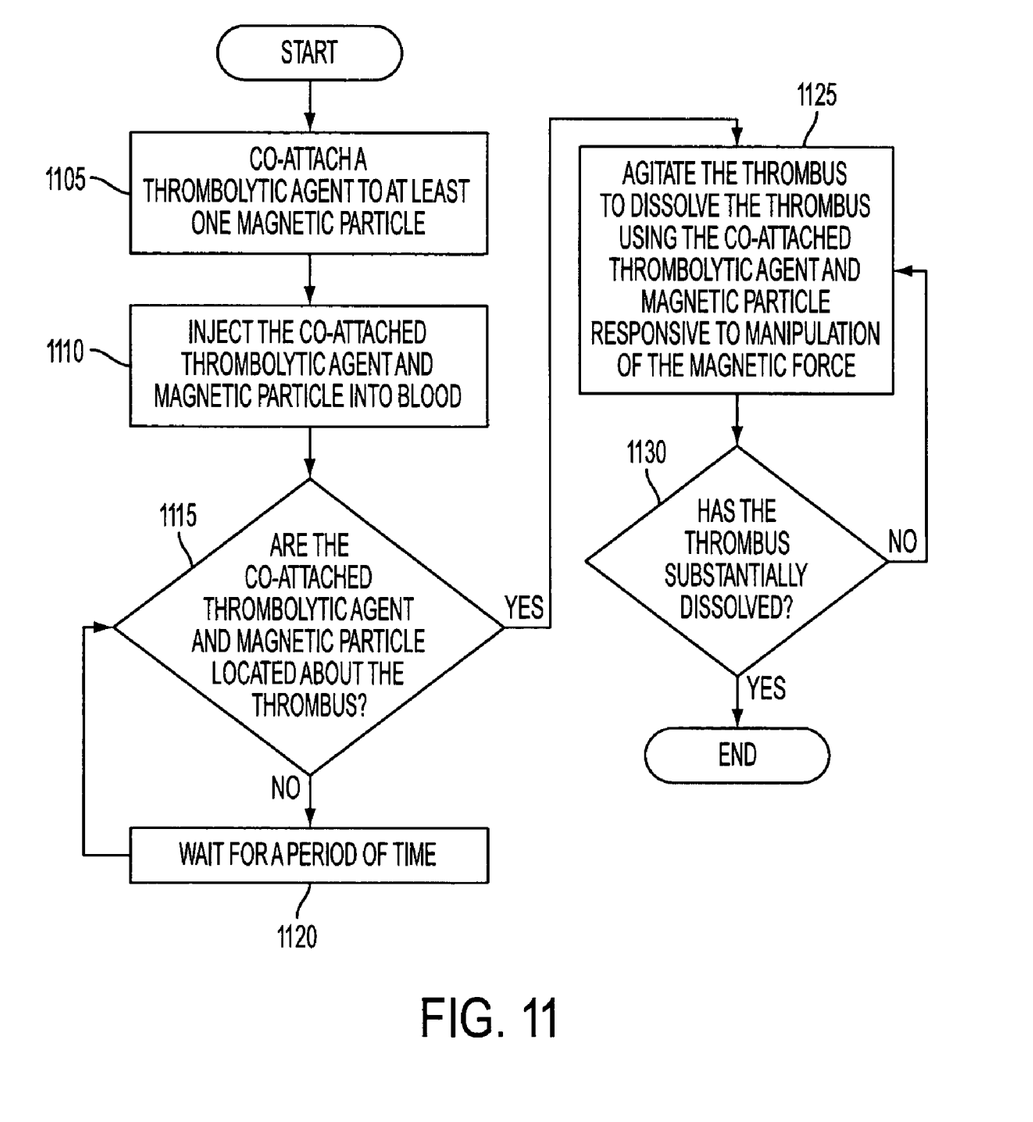
FIG. 11 shows a flow diagram illustrating another embodiment of a thrombolysis technique.

FIG. 11 shows a flow diagram illustrating still another thrombolysis technique according to some embodiments. At 1105, a drug manufacturer may co-attach a thrombolytic agent to at least one magnetic particle. The operator may inject the co-attached thrombolytic agent and magnetic particle either continuously or intermittently into blood (e.g., a bloodstream) of a patient. Preferably, the co-attached thrombolytic agent and magnetic particle are injected continuously through an IV. At 1115, a determination can be made whether the co-attached thrombolytic agent and magnetic particle are located about the thrombus.

If it is determined that the co-attached thrombolytic agent and the magnetic particle are not sufficiently located about the thrombus, the operator may wait for a period of time at 1120, after which the determination at 1115 can again be made. Alternatively, an inference can be made that after a predefined period of time, the co-attached thrombolytic agent and the magnetic particle are assumed to be located about the thrombus, without making an affirmative determination of such, and the method may then proceed to 1125.

At 1125, the operator may agitate the thrombus to dissolve the thrombus using the co-attached thrombolytic agent and the magnetic particle responsive to manipulation of the magnetic force. In other words, magnetic fields may exert a magnetic force to manipulate the co-attached thrombolytic agent and the magnetic particle, which may be coupled to the thrombus. The manipulation of the magnetic particle may agitate the thrombus and increase the rate of dissolution of the thrombus, which may further dissolve in the presence of the thrombolytic agent.

At 1130, a determination can be made whether the thrombus has substantially dissolved, and if so, the procedure may end. Otherwise, the procedure may return to 1125 to agitate the thrombus further.

Figure 12:
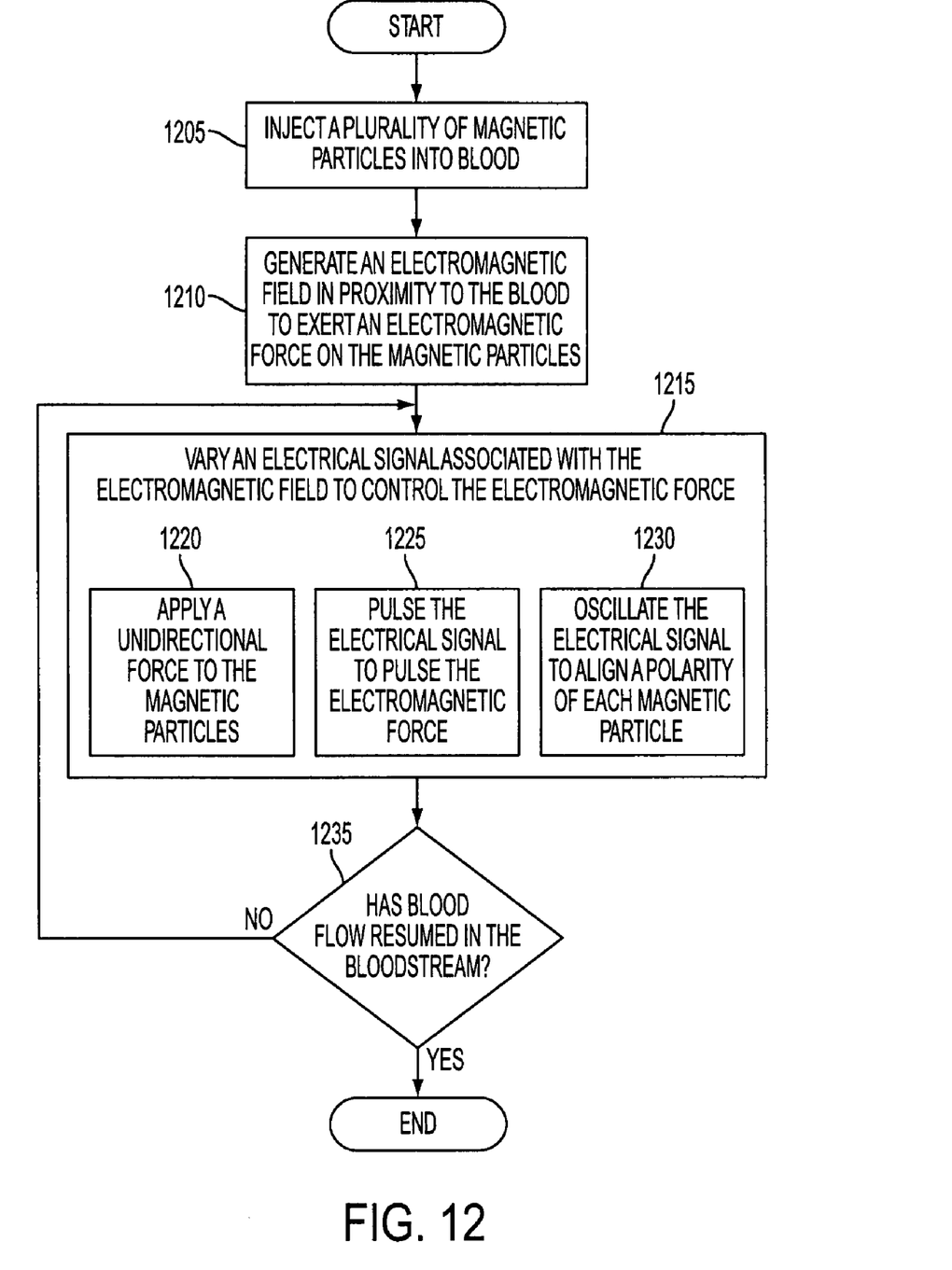
FIG. 12 shows a flow diagram illustrating another embodiment of a thrombolysis technique.

FIG. 12 shows a flow diagram illustrating another thrombolysis technique according to some embodiments. At 1205, an operator may inject a plurality of magnetic particles either continuously or intermittently into blood (e.g., a bloodstream) of a patient. Preferably, the magnetic particles are injected continuously through an IV. At 1210, the operator may cause the generation of an electromagnetic field in proximity to the blood to exert an electromagnetic force on the magnetic particles. At 1215, the operator (or an electromagnetic machine itself) may cause a variation in an electrical signal associated with the electromagnetic field to control the electromagnetic force.

Several variations may be employed. For example, at 1220, a unidirectional force may be applied to the magnetic particles. Another example may include pulsing (1225) the electrical signal to pulse the electromagnetic force. Yet another example may include oscillating (1230) the electrical signal to align a polarity of each magnetic particle. Persons having skill in the art will recognize that other approaches for manipulating the magnetic particles may be used. The various approaches are used for the purpose of further causing the breaking apart or the dissolution of the thrombus to allow a resumption or increase of blood flow.

At 1235, a determination can be made whether blood flow has resumed in the bloodstream. If such blood flow has sufficiently resumed, the procedure can end. Otherwise, the procedure can return to 1215 for additional application of the electromagnetic force to further break apart or dissolve the thrombus.

It will be appreciated that various of the above-disclosed and other features and functions, or alternatives thereof, may be desirably combined into many other different systems or applications. For example, some aspects of the invention may include a device comprising a magnet having a magnetic field capable of applying a magnetic force to manipulate a plurality of bioconjugated magnetic particles biochemically attached to thrombus-related proteins beneath a surface of the patient's body to the region of the thrombus. As another example, a method for performing a pharmaceutical therapy may comprise attaching magnetic particles to an intravenous material, and applying at least one of a static and a variable force to the magnetic particles to perform at least one of breaking apart, moving, and agitating the intravenous material. Various presently unforeseen or unanticipated alternatives, modifications, variations, or improvements therein may be subsequently made by those skilled in the art which are also intended to be encompassed by the following claims.

What is claimed is:

1. A method for affecting a thrombus after ischemic stroke, comprising:
   injecting a plurality of magnetic particles into blood; and
   affecting the thrombus using a magnetic force to manipulate the plurality of magnetic particles in the blood,
   wherein affecting the thrombus includes at least one of moving the thrombus and distorting the thrombus.

2. The method of claim 1, wherein injecting the plurality of magnetic particles includes injecting superparamagnetic particles, and wherein affecting the thrombus further includes manipulating the magnetic particles in the blood using the magnetic force.

3. The method of claim 2, further comprising:
   before injecting the superparamagnetic particles, conjugating the superparamagnetic particles to a thrombus-specific attachment agent;
   after a predetermined period of time, locating the thrombus-specific attachment agent and the magnetic particles about tissue of the thrombus; and
   breaking apart the thrombus by manipulating the superparamagnetic particles.

4. The method of claim 2, further comprising:
   before injecting the superparamagnetic particles, conjugating the superparamagnetic particles to a thrombus-specific attachment agent;
   after waiting a predefined period of time after injecting the superparamagnetic particles, inferring that the thrombus-specific attachment agent and the superparamagnetic particles are located about tissue of the thrombus; and
   breaking apart the thrombus by manipulating the superparamagnetic particles located about the thrombus.

5. The method of claim 4, wherein the thrombus-specific attachment agent comprises at least one anti-fibrin antibody structured to attach to the thrombus.

6. The method of claim 1, further comprising:
   injecting a thrombolytic agent into the blood to interact with the thrombus; and
   agitating the thrombus after injecting the thrombolytic agent to dissolve at least a portion of the thrombus using the magnetic force.

7. The method of claim 6, further comprising:
before injecting the thrombolytic agent, conjugating the thrombolytic agent to a thrombus-specific attachment agent.

8. The method of claim 6, wherein the thrombolytic agent comprises tissue plasminogen activator (tPA).

9. The method of claim 1, wherein affecting the thrombus further comprises moving a magnet having a magnetic field in proximity to the blood to exert the magnetic force on the plurality of magnetic particles.

10. The method of claim 1, wherein the magnetic force is an electromagnetic force generated using one or more electromagnets, and the method further comprises generating an electromagnetic field in proximity to the blood to exert the electromagnetic force on the magnetic particles.

11. The method of claim 10, further comprising varying an electrical signal associated with the electromagnetic field to control the electromagnetic force.

12. The method of claim 11, further comprising pulsing the electrical signal associated with the electromagnetic field to pulse the electromagnetic force.

13. A method for affecting a thrombus after ischemic stroke, comprising:
injecting a plurality of magnetic particles into blood, wherein the magnetic particles are conjugated to the thrombus-specific attachment agent and located about the tissue of the thrombus;
affecting the thrombus using a magnetic force to manipulate the plurality of magnetic particles in the blood; and
trapping the plurality of magnetic particles about the thrombus using the magnetic force.

14. A method for affecting a thrombus after ischemic stroke, comprising:
injecting a plurality of magnetic particles into blood;
affecting the thrombus using a magnetic force to manipulate the plurality of magnetic particles in the blood, wherein the magnetic force is an electromagnetic force generated using one or more electromagnets;
generating an electromagnetic field in proximity to the blood to exert the electromagnetic force on the magnetic particles;
varying an electrical signal associated with the electromagnetic field to control the electromagnetic force; and
wherein the magnetic force comprises a unidirectional magnetic force, the method further comprising:
applying the unidirectional magnetic force to the plurality of magnetic particles, wherein applying the unidirectional magnetic force includes at least one of compressing and moving the thrombus to allow the blood to resume flowing.

15. A method for affecting a thrombus after ischemic stroke, comprising:
injecting a plurality of magnetic particles into blood;
affecting the thrombus using a magnetic force to manipulate the plurality of magnetic particles in the blood, wherein the magnetic force is an electromagnetic force generated using one or more electromagnets;
generating an electromagnetic field in proximity to the blood to exert the electromagnetic force on the magnetic particles;
varying an electrical signal associated with the electromagnetic field to control the electromagnetic force; and
oscillating the electrical signal associated with the electromagnetic field to align a polarity of each of the plurality of magnetic particles so that the magnetic particles spin.

* * * * *